(12) United States Patent
Veress (10) Patent No.: US 10,799,511 B2
(45) Date of Patent: *Oct. 13, 2020

(54) METHODS FOR REDUCING OR AMELIORATING MORTALITY AND/OR MORBIDITY DUE TO CHLORINE INHALATION

(71) Applicant: THE REGENTS OF THE UNIVERSITY OF COLORADO, A BODY CORPORATE, Denver, CO (US)

(72) Inventor: Livia A. Veress, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/104,385

(22) Filed: Aug. 17, 2018

(65) Prior Publication Data

US 2019/0054092 A1 Feb. 21, 2019

Related U.S. Application Data

(60) Provisional application No. 62/547,588, filed on Aug. 18, 2017.

(51) Int. Cl.
*A61K 31/5517* (2006.01)
*A61P 39/00* (2006.01)

(52) U.S. Cl.
CPC .......... *A61K 31/5517* (2013.01); *A61P 39/00* (2018.01)

(58) Field of Classification Search
CPC .................................................. A61K 31/5517
USPC ........................................................ 514/220
See application file for complete search history.

(56) References Cited

PUBLICATIONS

"Chemical Treatment Guide: YELLOW," Joint EMS Protocols accessed online at www.jointemsprotocols.com/content/chemical-treatment-guide-yellow on Jul. 6, 2017.
Myers, et al., "Chlorine Inhalation in a Pediatric Patient," Journal of Emergency Nursing, vol. 23, Issue 6, Dec. 1997, pp. 583-585.

*Primary Examiner* — Kevin E Weddington
(74) *Attorney, Agent, or Firm* — Saul Ewing Arnstein & Lehr LLP; Kathryn Doyle; Domingos J. Silva (57) ABSTRACT

The present invention includes compounds, compositions and methods for reducing or ameliorating mortality and/or morbidity due to chlorine inhalation.

17 Claims, 10 Drawing Sheets

FIG. 1A

- Posture
    - 0 – normal
    - 1 – low posture
    - 2 – laying on the ground, not leaning
    - 3 – laying on the ground, leaning sideways
- Movement
    - 0 – normal
    - 1 – wobbling gait
    - 2 – wobbling gait, and falls
- Seizure
    - 0 – none
    - 1 – twitches/shuddering
    - 2 – actively seizing
- Tone
    - 0 – normal
    - 1 – mildly hypotonic
    - 2 – moderately hypotonic
    - 3 – severely hypotonic

FIG. 5A
Baseline before Cl₂ exposure

FIG. 5B
After Cl₂ exposure (30min) spike and wave with ataxia

FIG. 5C
After Cl₂ exposure (2h) repetitive epileptiform discharges

METHODS FOR REDUCING OR AMELIORATING MORTALITY AND/OR MORBIDITY DUE TO CHLORINE INHALATION

CROSS-REFERENCE TO RELATED APPLICATIONS

The present application claims priority under 35 U.S.C. § 119(e) to U.S. Provisional Application No. 62/547,588, filed Aug. 18, 2017, which application is hereby incorporated by reference in its entirety herein.

STATEMENT REGARDING FEDERALLY SPONSORED RESEARCH OR DEVELOPMENT

This invention was made with government support under R21 ES026830 awarded by the National Institutes of Health. The government has certain rights in the invention.

BACKGROUND OF THE INVENTION

Chlorine gas (also referred to as chlorine or $Cl_2$ herein) is one of the most common substances involved in toxic inhalation injury, either from accidental exposure or from deliberate dispersal as a chemical weapon. Chlorine gas was first used in 1915 as a chemical weapon at Ypres, France, during World War I, and has been used on multiple occasions since then throughout history, because it is readily available. More recently, instability of governments in the Middle East (Iraq, Iran, Syria, Libya, and now ISIS) has resulted in an unprecedented increase in chemical weapon, particularly chlorine gas. In the ongoing Syrian Civil War, the intentional use of chlorine to cause widespread casualties was seen in the towns of Kafr Zita, Harasta and Damascus in April 2014, among multiple similar reports. As the war continues in that region, more chemical attacks are expected.

These world events raise concerns that chlorine will be utilized more frequently in the near future as a weapon of opportunity by terrorists, globally as well as in the U.S. The Department of Homeland Security (DHS) has identified chlorine to be one of the highest terrorist threat agents within the U.S. boundaries, due to its availability, low cost, and high volume of transport via public routes. Additionally, numerous reports of industrial and occupational accidents involving chlorine gas exist, causing a wide range of human injury findings, including death. For all these reasons, the Public Health Emergency Medical Countermeasure Enterprise (PHEMCE) and the Department of Health and Human Services (HHS) are greatly concerned about the lack of effective antidotes or rescue therapies for chlorine-associated injury, particularly one that would improve survival and prevent serious morbidity after a significant exposure event.

Chlorine is a highly reactive gas with a density two times greater than air, and thus has propensity to settle near the ground. Chlorine is a potent respiratory and pulmonary irritant, with resultant dose-dependent injury severity after exposure. It reacts with water in the mucus membranes and airways to form both a strong acid (hydrochloric acid or HCl), and a powerful oxidant (hypochlorous acid or HOCl) at a 1:1 ratio, leading to acute inflammation of the conjunctiva, nasal mucosa, pharynx, larynx, trachea, and bronchi. Chlorine also reacts directly with organic materials within the tissues, to form oxidized and chlorinated derivatives that have further destructive potential, such as chlorotyrosine and other chlorinated amines. Current literature postulates that chlorine exerts its toxic effects on human tissues via several possible mechanisms. In one aspect, respiratory mucosa acidification by HCl and oxidative injury by HOCl have been implicated, as well as antioxidant depletion by both compounds within the airway lining. This then may lead to pulmonary inflammation, i.e. neutrophil influx within 6 hours (in mice), and a concomitant increase in airways hyperactivity by 24 hours. Use of some steroids can dampen this inflammatory response. In another aspect, tissue oxidation and destruction has also been shown to occur through chlorination of protein residues within tissues, with the resultant formation of chlorotyrosine and other chlorinated amines.

The clinical picture associated with acute chlorine inhalation includes initial throat and eye irritation, with progression to bronchoconstriction and tracheobronchitis manifesting as cough, wheezing and marked shortness of breath. Additional symptoms of cough, hemoptysis, fever, nausea, vomiting, syncope, and convulsions can also occur, with severity of symptoms depending on the dose of chlorine inhaled. Exposure to massive doses of chlorine results in profound hypoxemia, acute lung injury, with potential for interstitial pneumonia, pulmonary edema, pulmonary hypertension, decreased cardiac performance, myocardial infarction and death due to cardiopulmonary failure. Autopsy reports of humans inhaling a fatal dose of chlorine, report necrotizing tracheobronchitis, purplish red and firm lung parenchyma, and cardiomegaly as the primary findings, with the cause of death reported as asphyxiation. Animal models of massive chlorine inhalation in the anesthetized and ventilated pig have reported low cardiac output, bradycardia, high pulmonary artery pressures, and decreased ventricular stroke volume present immediately after exposure, often resulting in cardiovascular collapse within 6 hours after exposure. Chronic effect of chlorine in survivors are conflicting, with most human survivors demonstrating no consistent pattern of pulmonary function or other deficits. Most victims survive with only transient impairment.

To date, therapies focusing on the reversal of acute cardiopulmonary compromise after massive chlorine exposure have been scarce. Current treatment of acute chlorine inhalation, after prompt decontamination, is merely symptomatic: supplemental oxygen, inhaled bronchodilators, and positive pressure or mechanical ventilation after intubation in severely hypoxemic patients. Fluid supplementation may be useful, except if acute respiratory distress syndrome (ARDS) has developed. While corticosteroids have been recommended in the literature, based on either animal models or human case reports, they are not recommended by others due to insufficient clinical trials. Sodium bicarbonate nebulization has been tried in a limited number of patients, and while its effects in anecdotal reports were mainly beneficial, its use is limited due to hypothetical risks and lack of clinical trials. No therapy exists to prevent mortality after massive chlorine inhalation injury.

There is thus a need in the art for compositions and methods for reducing or ameliorating mortality and/or morbidity due to chlorine inhalation. The present invention addresses these needs.

BRIEF SUMMARY OF THE INVENTION

In one aspect, the invention provides a method of reducing and/or ameliorating mortality and/or morbidity due to chlorine inhalation in a subject, the method comprising administering to the subject a therapeutically effective amount of midazolam, or a salt, solvate, or tautomer thereof.

In certain embodiments, the midazolam is administered orally, buccally, intramuscularly, intravenously, or intranasally to the subject. In other embodiments, the midazolam is administered intramuscularly to the subject.

In certain embodiments, the midazolam is administered within 15 minutes to the subject after the subject is subjected to chlorine inhalation. In other embodiments, the midazolam is further administered to the subject about 15-60 minutes after the subject is subjected to chlorine inhalation.

In certain embodiments, the midazolam is administered at a dose ranging from about 0.016-1.66 mg/kg in humans. In other embodiments, the midazolam is administered to a human at a dose of about 0.016 mg/kg, 0.025 mg/kg, 0.033 mg/kg, 0.083 mg/kg, 0.16 mg/kg, 0.32 mg/kg, 0.5 mg/kg, 0.66 mg/kg, 0.83 mg/kg, 1 mg/kg, 1.16 mg/kg, 1.33 mg/kg, 1.5 mg/kg, and/or 1.66 mg/kg. In yet other embodiments, the midazolam is administered to a human at a dose of about 0.16 mg/kg.

In certain embodiments, the subject is further administered at least one agent selected from the group consisting of atropine and scopolamine, or a salt, solvate, geometric isomer, enantiomer, and/or diastereoisomer thereof. In other embodiments, the atropine is administered intravenously or intramuscularly to the subject. In yet other embodiments, the atropine is administered intramuscularly to the subject. In yet other embodiments, the scopolamine is administered intranasally, intravenously or intramuscularly to the subject. In yet other embodiments, the scopolamine is administered intramuscularly to the subject. In yet other embodiments, the midazolam and the agent are co-administered to the subject. In yet other embodiments, the midazolam and the agent are coformulated.

In certain embodiments, the subject experiences at least one effect selected from the group consisting of: increases survival, increases cardiac output, increases stroke volume, increases heart rate, helps normalize blood pH, helps normalize blood $pCO_2$, and improve neuromuscular tone.

In certain embodiments, the subject experiences at least one effect selected from the group consisting of: increases survival, helps normalize blood pH, and helps normalize blood $pCO_2$.

In certain embodiments, the subject experiences at least one effect selected from the group consisting of: increases survival, and reduces epileptiform activity.

In certain embodiments, the subject is a mammal. In other embodiments, the mammal is a human.

In another aspect, the invention provides a pharmaceutical composition comprising an amount of midazolam, or a salt, solvate, or tautomer thereof, which, when administered to a subject subjected to chlorine inhalation, reduces and/or ameliorates mortality and/or morbidity due to chlorine inhalation in the subject.

In certain embodiments, the pharmaceutical composition further comprises at least one agent selected from the group consisting of atropine and scopolamine, or a salt, solvate, geometric isomer, enantiomer, and/or diastereoisomer thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2 illustrates a pentylenetetrazole (PTZ) study, which can be used to assess CNS (central nervous system) excitability and GABA activity. PTZ is a non-competitive GABA agonist, which is administered IP at 50 mg/kg. Immediately after injection, the stop-watch is started and the following are recorded: (1) time of onset of seizure (around 60 seconds), and (2) duration of seizure (around 60 seconds). Score: 0, no seizure; 1, eye or facial twitches; 2, convulsive waves across body; 3, myoclonic jerks or rearing; 4, turn over to one side position; 5, turn over onto back position, generalized tonic-clonic seizures, or die during experiments.

FIGS. 4A-4C illustrate electroencephalogram (EEG) traces.

DETAILED DESCRIPTION OF THE INVENTION

The present invention relates, in one aspect, to the unexpected discovery that administration of midazolam to a subject with severe chlorine inhalation exposure improves the overall condition of the subject, including its survival rate. In certain embodiments, midazolam is administered orally, buccally, intramuscularly, intravenously, or intranasally to the subject. In other embodiments, midazolam is administered intramuscularly to the subject.

As described herein, therapeutic agents were tested for their ability to stabilize and/or rescue animals exposed to toxic inhalational levels of chlorine. Several of those agents proved to be ineffective, and in some cases even worsened the animal's overall condition: AEOL 10150 (manganese (III)meso-tetrakis(N,N'-diethyl-1,3-imidazolium-2-yl)porphyrin), SCN (a thiocyanate), Sodium Bicarbonate, Racemic epinephrine, Dexamethasone, Albuterol, iNO (inhaled nitric oxide), 2-PAM, Dextrose infusion, Bosantan, Dobutamine, Cyclosporine, Ranolazine, Pimonidazole, and Cobinamide.

Surprisingly, midazolam, atropine and scopolamine were found to have beneficial effects on animals exposed to high inhalational levels of chlorine. In certain embodiments, administration of at least one of these agents has at least one of these effects on chlorine-exposed animals: increases survival, increases cardiac output, increases stroke volume, increases heart rate, helps normalize blood pH, helps normalize blood $pCO_2$, and improve neuromuscular tone. In other embodiments, administration of at least one of these agents has at least one of these effects on chlorine-exposed animals: increases survival, helps normalize blood pH, and helps normalize blood $pCO_2$. In yet other embodiments, administration of at least one of these agents has at least one of the these effects on chlorine-exposed animals: increase survival, and decrease chlorine exposure-associated epileptiform activity.

Chlorine is well known to affect the respiratory tract in a dose-dependent fashion. The hallmark of injury is an intense airway injury, with potential for progression to acute lung injury (ALI) with hypoxemia, and possible development ARDS with higher dose exposures. Mortality after massive chlorine exposure occurs mostly within 4 hours after inhalation. However, the few fatal cases after chlorine exposure have shown massive cardiomegaly, relatively mild airway injury, and variable proximal and distal lung involvement. The cause of death is usually recorded to be from asphyxia of unclear mechanism.

As disclosed herein, chlorine gas is an extremely potent cholinesterase inhibitor similar to OP/CM agents, resulting in an overwhelming cholinergic state. Excess acetylcholine may lead to sustained activation of five muscarinic receptors ($M_1$-$M_5$), resulting in: water and electrolyte secretions ($M_1$); bradycardia and poor cardiac contractility ($M_2$); mucus secretion and bronchoconstriction ($M_3$); pulmonary vascular constriction ($M_3$); and systemic vasodilation ($M_3$). Signs of the cholinergic toxidrome may also include bradycardia, wheezing, rhinorrhea, rales, bronchoconstriction, respiratory depression, ataxia, and restlessness.

DEFINITIONS

As used herein, each of the following terms have the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics and chemistry are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, ±5%, ±1%, or ±0.1% from the specified value, as such variations are appropriate to perform the disclosed methods.

A disease or disorder is "alleviated" if the severity of a symptom of the disease or disorder, the frequency with which such a symptom is experienced by a patient, or both, is reduced.

As used herein, the term "atropine" refers to (3-endo)-8-methyl-8-azabicyclo[3.2.1]oct-3-yl 3-hydroxy-2-phenylpropanoate, or any salt, solvate, geometric isomer, enantiomer, and/or diastereoisomer thereof:

In one aspect, the terms "co-administered" and "co-administration" as relating to a subject refer to administering to the subject a compound of the invention, or a derivative, solvate, salt or prodrug salt thereof, along with a compound and/or composition that may also treat the disorders or diseases contemplated within the invention. In certain embodiments, the co-administered compounds and/or compositions are administered separately, or in any kind of combination as part of a single therapeutic approach. The co-administered compound and/or composition may be formulated in any kind of combinations as mixtures of solids and liquids under a variety of solid, gel, and liquid formulations, and as a solution.

A "disease" as used herein is a state of health of an animal wherein the animal cannot maintain homeostasis, and wherein if the disease is not ameliorated then the animal's health continues to deteriorate.

A "disorder" as used herein in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount" or "therapeutically effective amount" or "pharmaceutically effective amount" of a compound are used interchangeably to refer to the amount of the compound and/or composition which is sufficient to provide a beneficial effect to the subject to which the compound and/or composition is administered. The term to "treat," as used herein, means reducing the frequency with which symptoms are experienced by a patient or subject or administering an agent or compound to reduce the severity with which symptoms are experienced. An appropriate therapeutic amount in any individual case may be determined by one of ordinary skill in the art using routine experimentation.

The terms "inhibit" and "antagonize", as used herein, mean to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

"Instructional material," as that term is used herein, includes a publication, a recording, a diagram, or any other medium of expression which can be used to communicate the usefulness of the composition and/or compound of the invention in a kit.

The term "midazolam" refers to 8-chloro-6-(2-fluorophenyl)-1-methyl-4H-imidazo[1,5-a][1,4]benzodiazepine, or a salt, solvate, or tautomer thereof:

The terms "patient," "subject" or "individual" are used interchangeably herein, and refer to any animal, or cells thereof whether in vitro or in situ, amenable to the methods described herein. In a non-limiting embodiment, the patient, subject or individual is a human.

"Parenteral" administration of a composition includes, e.g., subcutaneous (s.c.), intravenous (i.v.), intramuscular (i.m.), or intrasternal injection, or infusion techniques.

As used herein, the term "pharmaceutical composition" refers to a mixture of at least one compound and/or composition useful within the invention with other chemical components, such as carriers, stabilizers, diluents, dispersing agents, suspending agents, thickening agents, and/or excipients. The pharmaceutical composition facilitates administration of the compound and/or composition to an organism. Multiple techniques of administering a compound and/or composition exist in the art including, but not limited to: intravenous, oral, aerosol, parenteral, ophthalmic, pulmonary, intracranial and topical administration.

As used herein, the term "pharmaceutically acceptable" refers to a material, such as a carrier or diluent, which does not abrogate the biological activity or properties of the composition, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt, prodrug, solvate or derivative of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

The term "prevent," "preventing" or "prevention," as used herein, means avoiding or delaying the onset of symptoms associated with a disease or condition in a subject that has not developed such symptoms at the time the administering of an agent or compound commences.

As used herein, the term "scopolamine" refers to (1R,2R,4S,5S,7s)-9-methyl-3-oxa-9-azatricyclo[3.3.1.02,4]nonan-7-yl (S)-3-hydroxy-2-phenylpropanoate, or any salt, solvate, geometric isomer, enantiomer, and/or diastereoisomer thereof:

By the term "specifically bind" or "specifically binds," as used herein, is meant that a first molecule (e.g., an antibody) preferentially binds to a second molecule (e.g., a particular antigenic epitope), but does not necessarily bind only to that second molecule.

As used herein, a "subject" refers to a human or non-human mammal. Non-human mammals include, for example, livestock and pets, such as ovine, bovine, porcine, canine, feline and murine mammals. In certain embodiments, the subject is human.

As used herein, the term "treatment" or "treating" is defined as the application or administration of a therapeutic agent, i.e., a composition useful within the invention (alone or in combination with another pharmaceutical agent), to a subject, or application or administration of a therapeutic agent to an isolated tissue or cell line from a subject (e.g., for diagnosis or ex vivo applications), who has a disease or disorder, a symptom of a disease or disorder or the potential to develop a disease or disorder, with the purpose to cure, heal, alleviate, relieve, alter, remedy, ameliorate, improve or affect the disease or disorder, the symptoms of the disease or disorder or the potential to develop the disease or disorder. Such treatments may be specifically tailored or modified, based on knowledge obtained from the field of pharmacogenomics.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Methods

The invention provides a method of reducing or ameliorating mortality and/or morbidity due to chlorine inhalation in a subject. In certain embodiments, the method comprises administering to the subject a therapeutically effective amount of midazolam, or a salt, solvate, or tautomer thereof.

In certain embodiments, midazolam is administered orally, buccally, intramuscularly, intravenously, or intranasally to the subject. In other embodiments, midazolam is administered intramuscularly to the subject.

In certain embodiments, the subject is further administered at least one agent selected from the group consisting of atropine and scopolamine, or a salt, solvate, geometric isomer, enantiomer, and/or diastereoisomer thereof.

In certain embodiments, atropine is administered intravenously or intramuscularly to the animal. In other embodiments, atropine is administered intramuscularly to the animal. In yet other embodiments, scopolamine is administered intranasally, intravenously or intramuscularly to the animal. In other embodiments, scopolamine is administered intramuscularly to the animal.

In certain embodiments, the midazolam and the at least one additional agent are co-administered to the subject. In other embodiments, the midazolam and the at least one additional agent are co-formulated.

In certain embodiments, the midazolam is administered within 15 minutes after the chlorine exposure. In other embodiments, the agent is further administered about 60 minutes after the chlorine exposure. In yet other embodiments, the midazolam is administered at a dose ranging from about 0.1-10 mg/kg in the rat. In yet other embodiments, based on Human Equivalent Dose (HED) calculations from FDA, the human-to-rat dose conversion rate is about 1:6.1. In yet other embodiments, the midazolam is administered at a dose ranging from about 0.016-1.66 mg/kg in humans. In yet other embodiments, each administration of the agent is independently performed at a dose of about 0.1 mg/kg, 0.15 mg/kg, 0.2 mg/kg, 0.5 mg/kg, 1 mg/kg, 2 mg/kg, 3 mg/kg, 4 mg/kg, 5 mg/kg, 6 mg/kg, 7 mg/kg, 8 mg/kg, 9 mg/kg, and/or 10 mg/kg to the rat. In yet other embodiments, each administration of the agent is independently performed at a dose of about 0.016 mg/kg, 0.025 mg/kg, 0.033 mg/kg, 0.083 mg/kg, 0.16 mg/kg, 0.32 mg/kg, 0.5 mg/kg, 0.66 mg/kg, 0.83 mg/kg, 1 mg/kg, 1.16 mg/kg, 1.33 mg/kg, 1.5 mg/kg, and/or 1.66 mg/kg to a human.

In certain embodiments, the compound and/or composition of the invention is administered by an intramuscular, inhalational, intranasal, oral, rectal, vaginal, parenteral, intracranial, topical, transdermal, pulmonary, buccal, ophthalmic, intrathecal, or intravenous route of administration.

Compositions and Combination Therapies

In certain embodiments, the compounds and/or compositions contemplated within the invention are useful within the methods of the invention in combination with at least one additional agent useful for treating or preventing a disease or disorder contemplated herein. This additional compound may comprise compounds identified herein or compounds, e.g., commercially available compounds, known to treat or prevent a disease or disorder contemplated herein.

A synergistic effect may be calculated, for example, using suitable methods such as, for example, the Sigmoid-$E_{max}$ equation (Holford & Scheiner, 1981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.1 and 5,000 mg/kg (or 0.1 and 5,000 U/kg) per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician, having ordinary skill in the art may readily determine and prescribe the effective amount of the pharmaceutical composition required. For example, the physician could start doses of the compounds of the invention employed in the pharmaceutical composition at levels lower than that required in order to achieve the desired therapeutic effect and gradually increase the dosage until the desired effect is achieved.

In certain embodiments, the compositions of the invention are formulated using one or more pharmaceutically acceptable excipients or carriers. In other embodiments, the pharmaceutical compositions of the invention comprise a therapeutically effective amount of a compound of the invention and a pharmaceutically acceptable carrier.

In certain embodiments, the compositions of the invention are administered to the patient by continuous infusion and/or in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 3050 μg to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In certain embodiments of a formulation for parenteral administration, the active ingredient is provided in dry (i.e., powder or granular) form for reconstitution with a suitable vehicle (e.g., sterile pyrogen free water) prior to parenteral administration of the reconstituted composition.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In certain embodiments, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of a disease or disorder contemplated in the invention. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the compound of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in humans. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Unless otherwise noted, all cell lines, starting materials and reagents were obtained from commercial suppliers and used without purification.

Example 1

Chlorine Exposure and Clinical Monitoring

Sprague-Dawley rats (290-340 g, male) were exposed for 30 minutes to 550 ppm of chlorine via whole-body exposure in a sealed 5-L cylindrical glass chamber (Specialty Glass Inc, Houston, Tex.). Heart rate and $SpO_2$ were obtained using a MouseOx (Starr Life Sciences) pulse oximeter collar. Respiratory rate (RR, bpm) was obtained manually every hour. Respiratory distress scores (0 to 6) and neuromuscular/ataxia scores (combined score of posture 0-3, tone 0-3, movement 0-2, seizure 0-2) were obtained hourly.

Video-Electroencephalogram (EEG)

Rats were implanted with cortical electroencephalographic (EEG) electrodes to monitor seizure activity, then allowed to recover for 1 week. Baseline EEG levels were obtained, followed by chlorine inhalation exposure, followed by 6 hours of continuous EEG monitoring using Stellate, Pinnacle and Triangle equipment. Data was reviewed and analyzed by staff neurophysiologist.

PTZ Testing

Pentylenetetrazole (50 mg/kg, i.p.) was given to induce seizures 30 min after $Cl_2$, and duration timed.

Drug Treatments

Midazolam (IM, 1 mg/kg) was given 15 min after chlorine exposure.

Comments

Figure 1A:
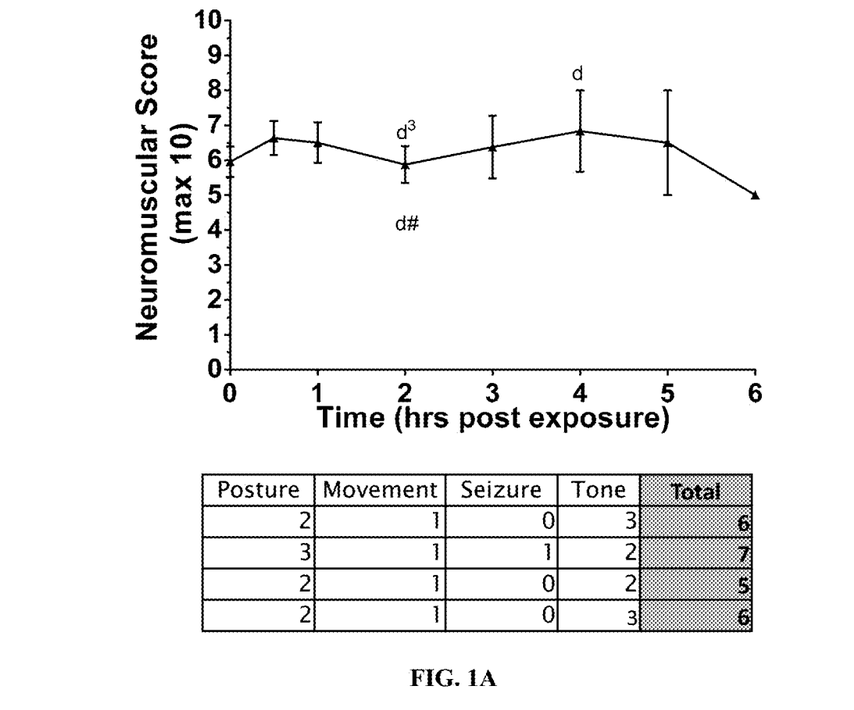
FIGS. 1A-1B illustrate an observational scoring for neuromuscular/ataxia score.
Figure 1B:
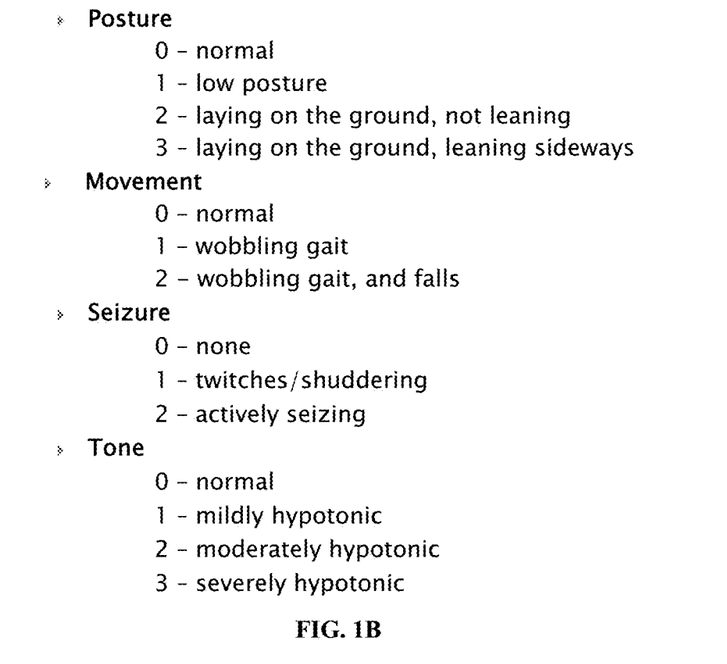
Figure 2:
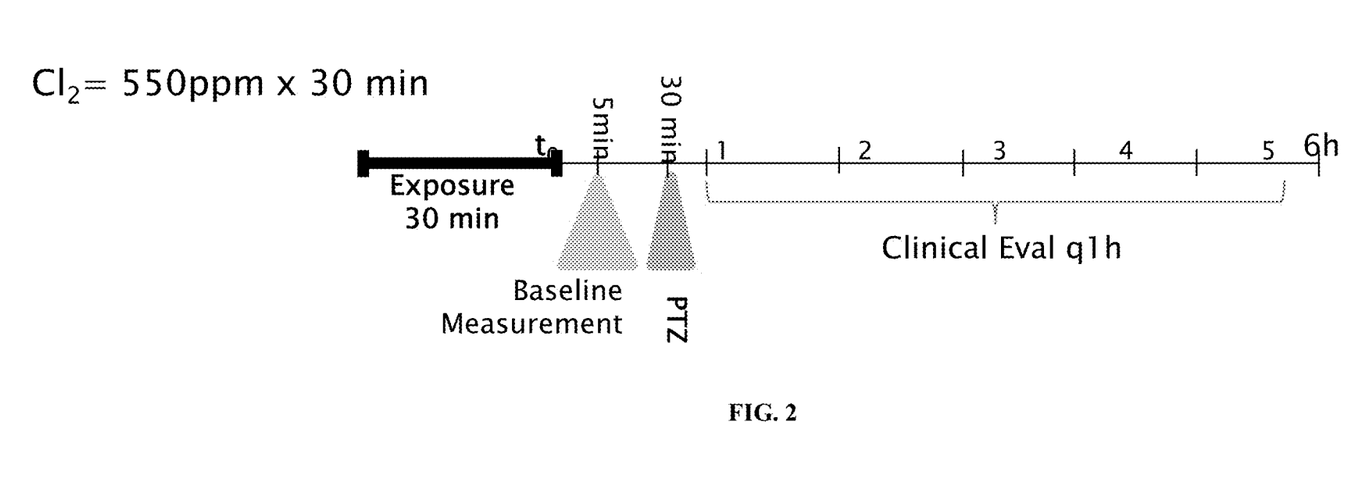
Figure 3A:
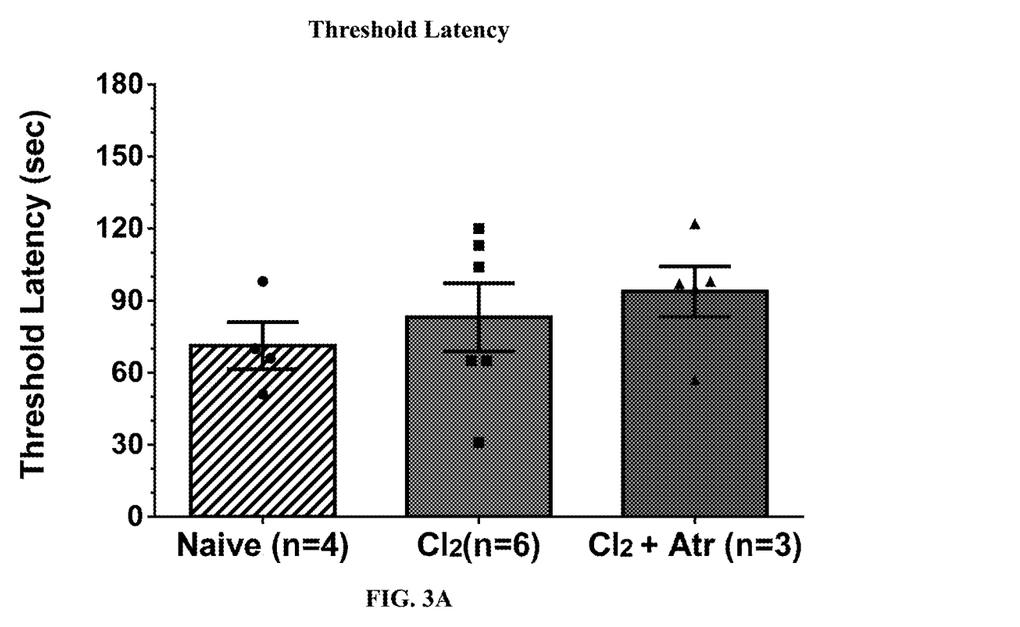
FIGS. 3A-3B illustrate a PTZ study. Chlorine did not lower seizure threshold, but caused diminished ability to stop seizures after onset (seizure propagation problem). Atropine had no effect in seizure duration reduction.
Figure 3B:
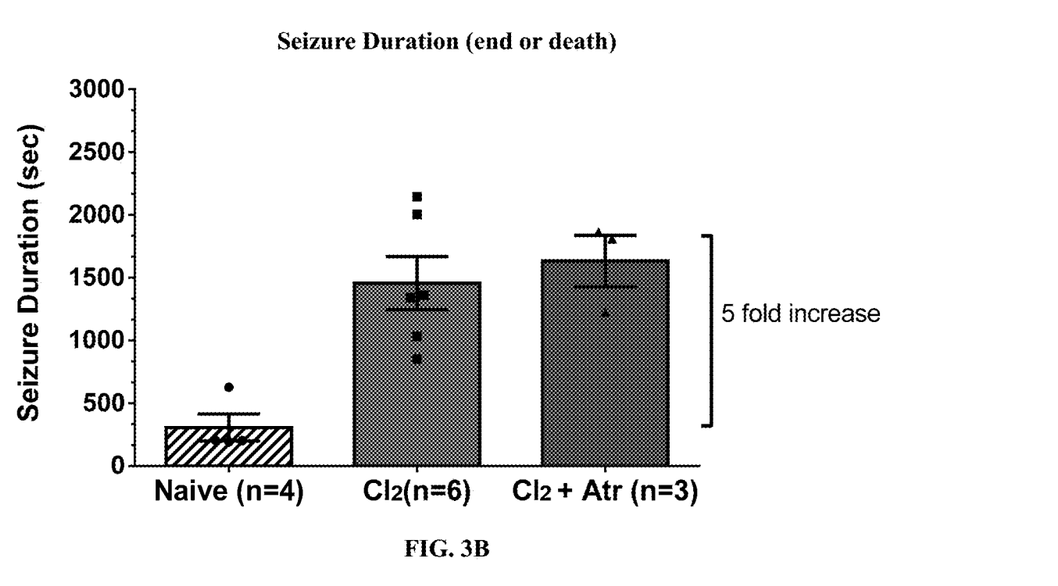
Figure 4A:
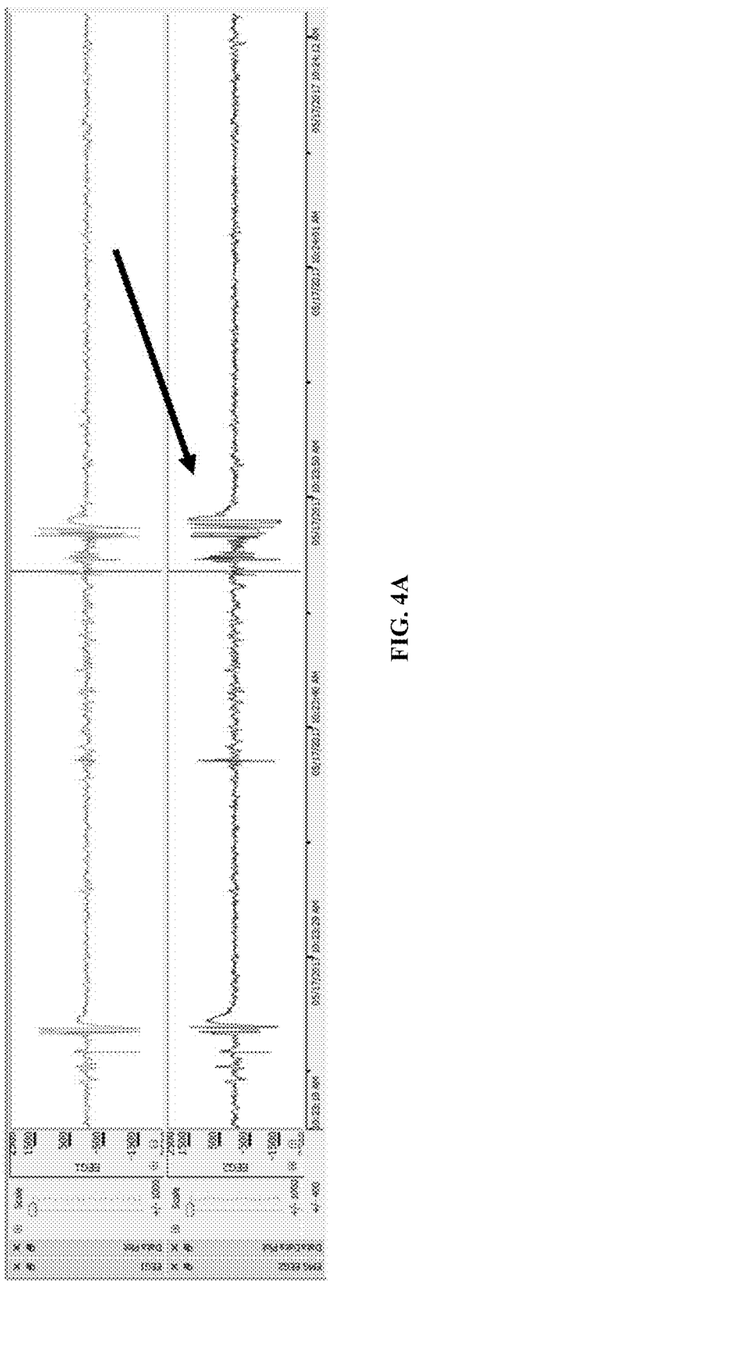
FIG. 4A: Spike and sharp wave, with left arm myoclonus, 30 min after exposure.
Figure 4B:
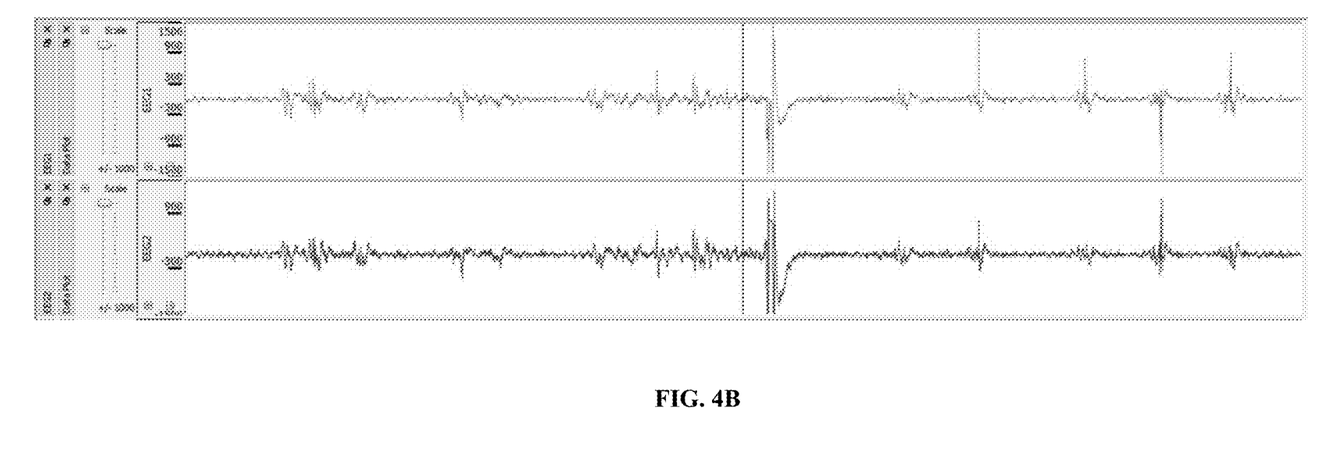
FIG. 4B: Ataxia, periodic lateral epileptiform discharges, 3 hours after exposure.
Figure 4C:
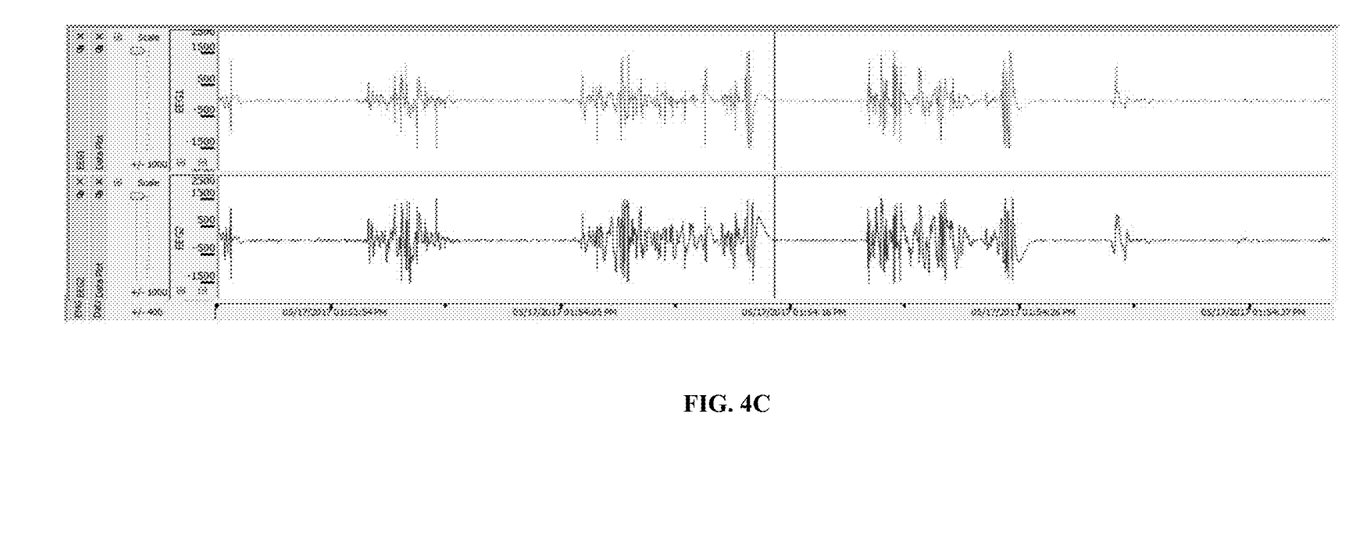
FIG. 4C: Epileptiform activity prior to death.
Figure 5A:
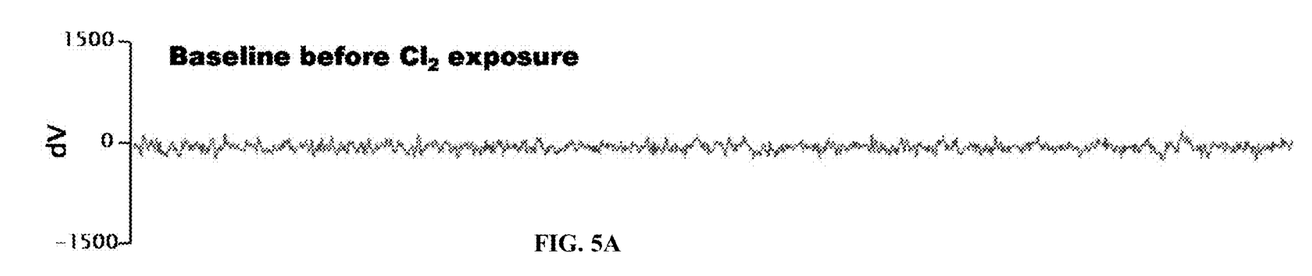
FIGS. 5A-5E illustrate chlorine-induced abnormal EEG. Midazolam clearly reduces epileptiform activity in the animals.
Figure 5B:
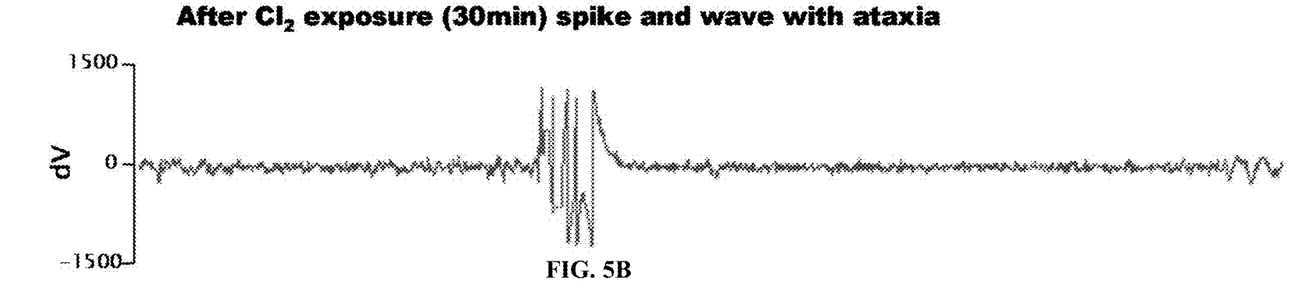
Figure 5C:
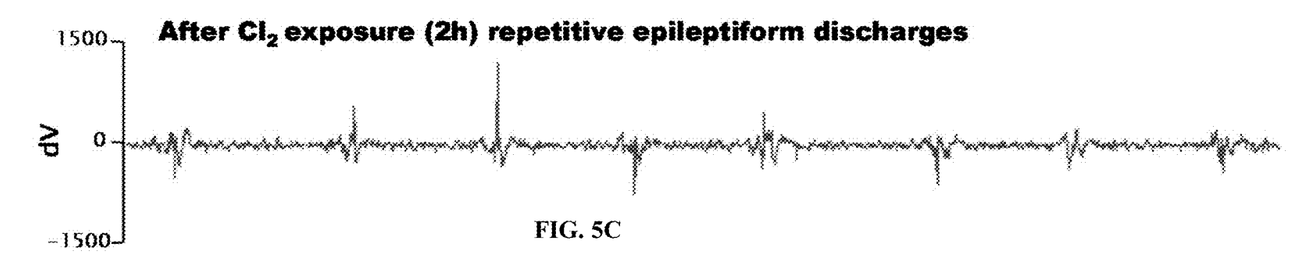
Figure 5D:
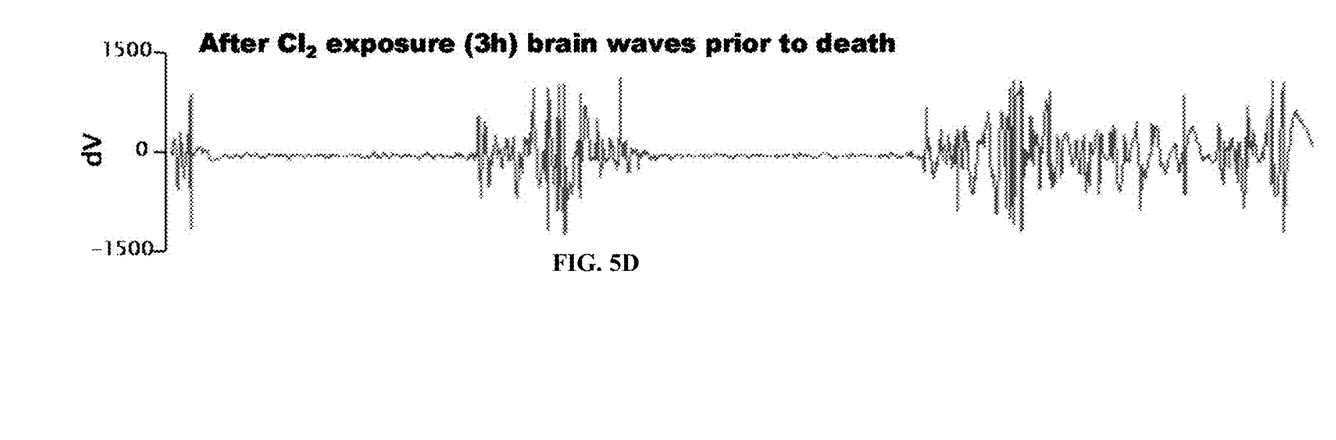
Figure 5E:
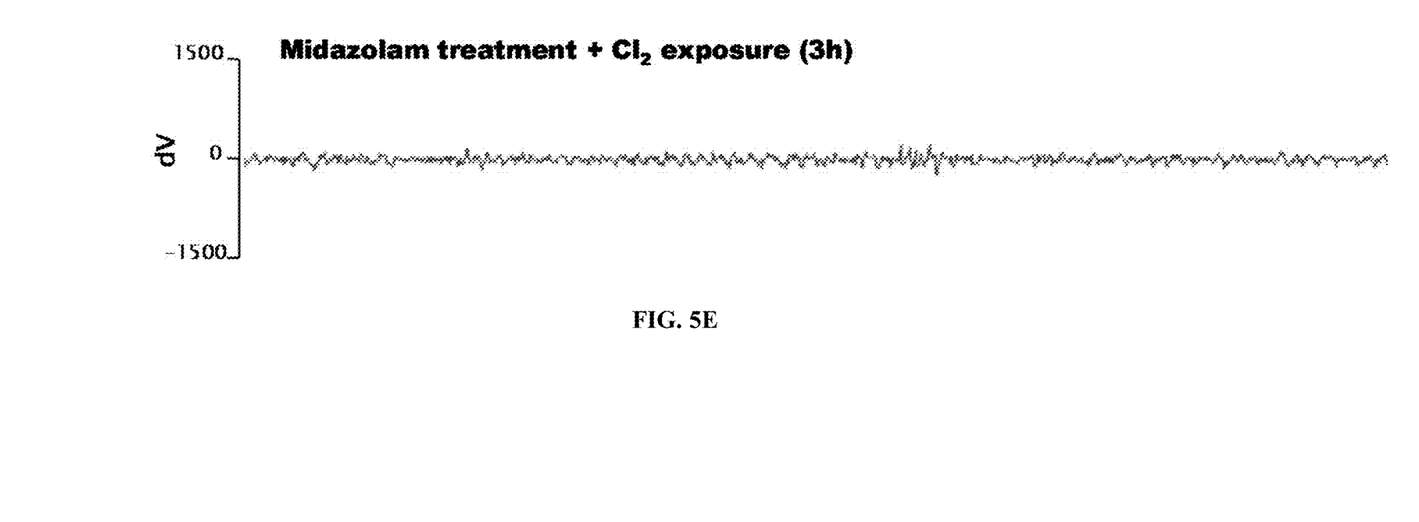
Figure 6:
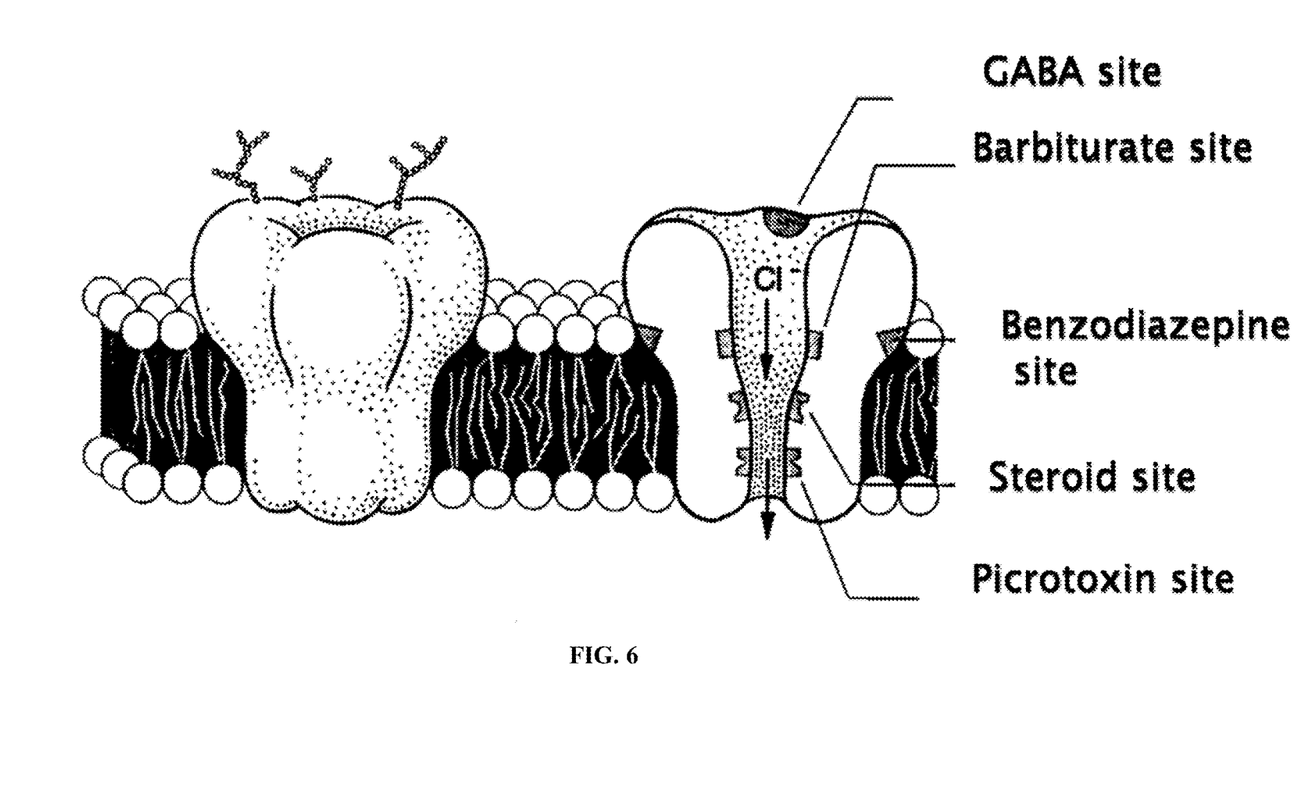
FIG. 6 is a schematic illustration of a $GABA_A$ receptor.

As illustrated in FIGS. 3A-3B, PTZ testing after chlorine exposure showed increased seizure duration, as compared to naïve animals. Atropine had no measurable effect in this model.

FIG. 5 illustrates brain EEG cortical activity during the experiment. Administration of midazolam decreased epileptiform activity caused by high dose chlorine inhalation.

Figure 7:
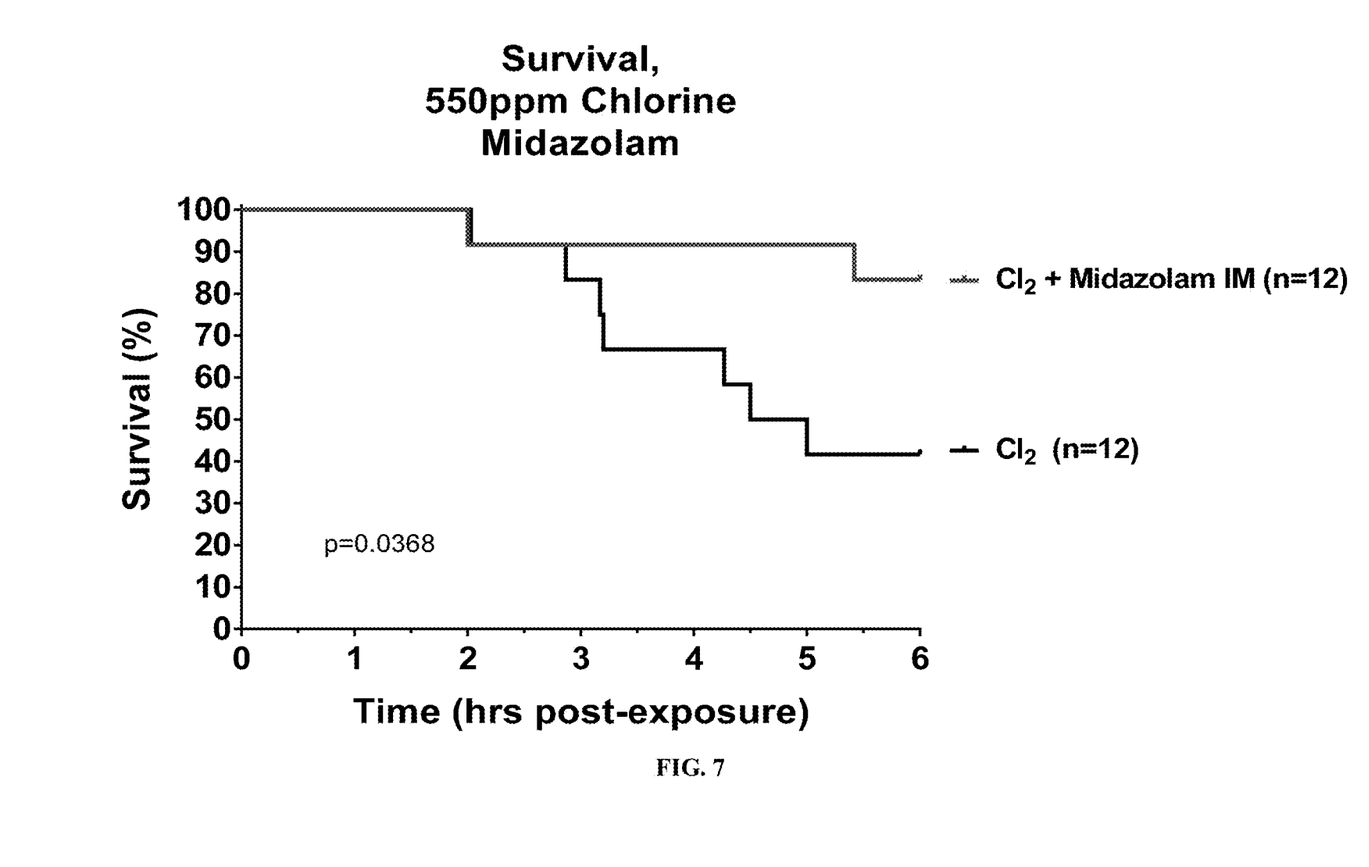
FIG. 7 comprises a graph illustrating the finding that midazolam improves survival after severe chlorine inhalation.

FIG. 7 illustrates survival data obtained in this experiment. Administration of midazolam nearly doubled the survival rate for animals exposed to severe chlorine inhalation conditions (83% vs. 42% for chlorine-only control animals).

TABLE 1

Thromboelastography 1 hour after 600 ppm chlorine

| Laboratory parameter | Naïve | Chlorine |
|---|---|---|
| Hb (g/dL) | 15.8 | 19.4 |
| PLTs (×10$^9$/L) | 845 | 940 |
| Arterial pH | 7.40 | 6.95 |
| Lactate (mmol/L) | 1.69 | 7.41 |
| TEG-SP (min) | 3.6 | 1.6 |
| TEG-R (min) | 3.8 | 1.7 |
| TEG-K (min) | 0.8 | 0.8 |
| TEG-α (deg) | 82 | 83.2 |
| TEG-MA (Kdyne/cm$^2$) | 75.8 | 72.3 |
| TEG-LY30 (%) | 0.9 | 1.8 |

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of reducing or ameliorating mortality or morbidity due to chlorine inhalation in a subject,
    the method comprising administering to the subject a therapeutically effective amount of midazolam, or a salt, solvate, or tautomer thereof, and optionally a therapeutically effective amount of at least one agent selected from the group consisting of atropine and scopolamine, or a salt, solvate, geometric isomer, enantiomer, or diastereoisomer thereof,
    wherein the midazolam and the optional agent are the only active ingredients administered to reduce or ameliorate mortality or morbidity due to chlorine inhalation in the subject.

2. The method of claim 1, wherein the midazolam is administered orally, buccally, intramuscularly, intravenously, or intranasally to the subject.

3. The method of claim 2, wherein the midazolam is administered intramuscularly to the subject.

4. The method of claim 1, wherein the midazolam is administered within 15 minutes to the subject after the subject is subjected to chlorine inhalation.

5. The method of claim 4, wherein the midazolam is further administered to the subject about 15-60 minutes after the subject is subjected to chlorine inhalation.

6. The method of claim 1, wherein the midazolam is administered at a dose ranging from about 0.016-1.66 mg/kg in humans.

7. The method of claim 6, wherein the midazolam is administered to a human at a dose of about 0.016 mg/kg, 0.025 mg/kg, 0.033 mg/kg, 0.083 mg/kg, 0.16 mg/kg, 0.32 mg/kg, 0.5 mg/kg, 0.66 mg/kg, 0.83 mg/kg, 1 mg/kg, 1.16 mg/kg, 1.33 mg/kg, 1.5 mg/kg, or 1.66 mg/kg.

8. The method of claim 6, wherein the midazolam is administered to a human at a dose of about 0.16 mg/kg.

9. The method of claim 1, wherein the subject is administered atropine intravenously or intramuscularly.

10. The method of claim 1, wherein the subject is administered scopolamine intranasally, intravenously or intramuscularly.

11. The method of claim 1, wherein the subject is co-administered_midazolam and the at least one agent.

12. The method of claim 11, wherein the midazolam and the at least one agent are coformulated.

13. The method of claim 1, wherein the subject experiences at least one effect selected from the group consisting of: increases survival, increases cardiac output, increases stroke volume, increases heart rate, helps normalize blood pH, helps normalize blood $pCO_2$, and improve neuromuscular tone.

14. The method of claim 1, wherein the subject experiences at least one effect selected from the group consisting of: increases survival, helps normalize blood pH, and helps normalize blood $pCO_2$.

15. The method of claim 1, wherein the subject experiences at least one effect selected from the group consisting of: increases survival, and reduces epileptiform activity.

16. The method of claim 1, wherein the subject is a mammal.

17. The method of claim 16, wherein the mammal is a human.

* * * * *